United States Patent
Becker

(10) Patent No.: US 6,183,514 B1
(45) Date of Patent: Feb. 6, 2001

(54) SELF POSITIONING BREAST PROSTHESIS

(76) Inventor: Hilton Becker, 5458 Town Center Rd., Suite 101, Medplex Building, Boca Raton, FL (US) 33486

( * ) Notice: Under 35 U.S.C. 154(b), the term of this patent shall be extended for 0 days.

(21) Appl. No.: 09/374,850

(22) Filed: Aug. 16, 1999

(51) Int. Cl.$^7$ ............................................. A61F 2/12
(52) U.S. Cl. ....................................................... 623/8
(58) Field of Search ................................... 623/7, 8

(56) References Cited

U.S. PATENT DOCUMENTS

| | | | |
|---|---|---|---|
| 3,934,274 | * | 1/1976 | Harltley, Jr. ............................. 623/8 |
| 4,773,909 | * | 9/1988 | Chaglassian ............................ 623/8 |
| 4,790,848 | * | 12/1988 | Cronin .................................... 623/8 |
| 4,944,749 | * | 7/1990 | Becker .................................... 623/8 |
| 5,246,454 | * | 9/1993 | Peterson ................................. 623/8 |

* cited by examiner

*Primary Examiner*—Michael J. Milano
*Assistant Examiner*—Brian E. Pellegrino
(74) *Attorney, Agent, or Firm*—Dorgherty & Troxell

(57) ABSTRACT

A dual lumen gravity oriented breast prosthesis or implant for surgical implantation includes inner and outer lumens which are defined by inner and outer closed envelopes of a medical grade elastomer. The outer closed envelope or lumen defines a generally oval or tear-shape with upper and lower portions. The outer envelope also contains a quantity of fluid material as for example a silicone gel having a first density. The prosthesis also includes a second or inner lumen defined by a second closed envelope of medical grade elastomer which is disposed in and fixed in the lower portion of the outer closed envelope. The inner lumen may be of various shapes such as generally spherical or preferably crescent shape. The second lumen is filled with a saline solution which has a density which is greater than the density in the outer lumen. The inner lumen with its greater density maintains or returns the prosthesis to its predetermined orientation when an individual in whom the prosthesis is implanted is in a standing or sitting position.

14 Claims, 3 Drawing Sheets

SELF POSITIONING BREAST PROSTHESIS

FIELD OF THE INVENTION

The present invention relates to an improved prosthesis and more particularly to a dual lumen gravity oriented breast implant.

BACKGROUND FOR THE INVENTION

Surgical reconstruction of a human breast as a result of injury or as a result of a partial or total mastectomy have been performed for many years. Such reconstruction may incorporate an inflatable implant including inner and outer lumens as for example disclosed in my earlier patent for an Implant and Inflating Construction U.S. Pat. No. 4,944,749 which is incorporated herein in its entirety by reference.

In the development of breast implants there has been an effort to provide a more lifelike substitute for the breast which has been removed. One approach is disclosed in the U.S. Patent of Cronin No. 4,790,848. As disclosed therein, a multiple lumen implant includes a spherically shaped inner lumen which is unattached and free floating. This approach provides a construction which maintains a high projection and at the same time is said to simulate the natural flow of breast tissue during a variety of activities in which an individual may participate on a daily basis.

A more recent approach in the development of implants is to manufacture implants which have an oval or tear-shape so that the implant approximates the shape of a natural breast. The problem with this approach is that once in place, the implants have a tendency to rotate within an individual's body. To overcome this problem, implants have been manufactured with a textured surface which tends to resist such movement. However, the textured surface does not provide the natural feel, movement and appearance of a smooth surface implant. Despite the textured surface, these implants still have a tendency to rotate.

Accordingly, it is presently believed that there is a relatively large market for an improved implant in accordance with the present invention. It is believed that there will be a demand for an improved implant that provides a more natural appearance and feel and at the same time tends to maintain the implant and return the implant to a natural position when the individual is in a standing, sitting or semi-reclining position.

BRIEF SUMMARY OF THE INVENTION

In essence, the present invention contemplates a self-positioning implant containing materials of different densities to enable the implant to remain anatomically positioned once surgically implanted within the human body. The prosthesis or breast implant includes an outer lumen, i.e. an outer closed envelope of medical grade elastomer that defines a preferably oval or generally tear-shape with upper and lower portions. The lower portion may be somewhat more rounded or fuller to more closely resemble the shape of a human breast. The outer lumen includes a first low density fluid material such as a silicon gel or hydrogel of a first given density contained therein.

The prosthesis also includes a second or inner lumen. The second or inner lumen comprises a closed envelope of medical grade elastomer which is disposed within the outer lumen. The second or inner lumen is fixed within a lower portion and preferably the lower quartile of the outer lumen and contains a second fluid material such as a saline solution of a given density which is greater than the density of the gel in the outer lumen.

The mammary prosthesis is then maintained or returned to its predetermined position by the higher density of the second fluid material which is contained in the lower portion of the outer chamber acting as a weight (similar to a sailboat keel).

The invention will now be described in connection with the accompanying drawings wherein like reference numerals have been used to designate like parts.

DESCRIPTION OF THE PREFERRED EMBODIMENTS OF THE INVENTION

Figure 1:
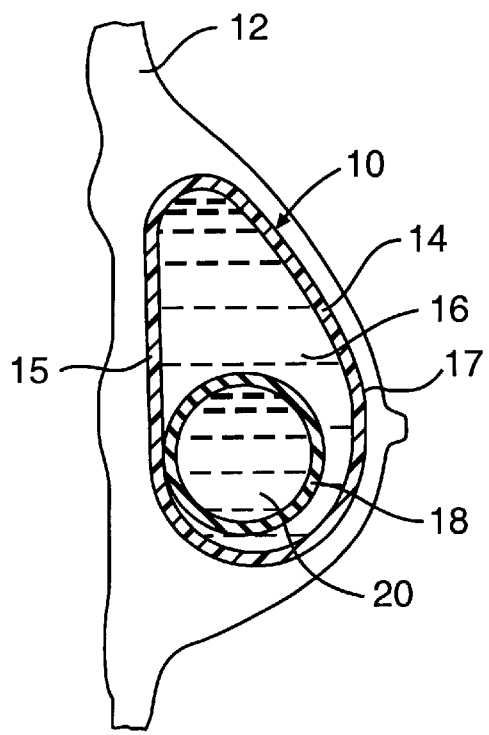
FIG. 1 is a schematic cross sectional view of a human breast which has been implanted with a mammary prosthesis in accordance with a first embodiment of the present invention.

Referring now to the drawings, a mammary prosthesis or breast implant 10 is shown as implanted in the breast tissue 12 of a patient. The implant 10 includes an outer envelope 14 of a medical grade elastomer such as silicone and a silicone gel 16 is contained within the outer envelope 14. The silicone gel 16 may be replaced by other suitable materials such as polyvinyl pyrralidone, hyaluronic acid, polyacrlimides and polysaccharides.

The walls of the lumen, i.e. the outer envelope 14 and inner envelope 18 may be made of various soft flexible biocompatible materials such as a silicone elastomer. Preferred materials include silicone elastomers such as polydimethylsiloxane or polymethylvinylsiloxane or copolymers thereof with other substances. Other polymers may be substituted as will be apparent to those skilled in the art.

As illustrated, the outer envelope 14 has an oval or generally tear-shape with a relatively flat rear portion 15 and rounded dome or a forward surface 17. The outer envelope 14 defines an outer lumen which may be of a generally tear-drop shape or other non-symmetrical shape in order to conform to the contours of a human breast. It should be recognized that in certain cases a round shape may be needed.

The implant 10 also includes an inner lumen which is defined by an inner envelope 18. This inner envelope 18 is preferably of the same medical grade elastomer as the outer envelope 14. The inner envelope 18 may be of a substantially spherical shape as illustrated in FIG. 1 and is fixed in a lower portion of the outer lumen by conventional means as will be well understood by a person of ordinary skill in the art of designing and manufacturing surgical implants.

The inner lumen or inner envelope 18 also contains a fluid 20 such as a saline solution which has a density which is greater than the density of the gel in the outer lumen. It is an important aspect of the present invention that the inner lumen is fixed in a lower portion of the outer lumen and that the center of gravity 18' of the saline filled inner lumen is sufficiently below the center of gravity of the outer lumen 14' so that the implant will be self-positioning. For example, in a preferred embodiment of the invention, the inner lumen is substantially contained within the lower portion of the outer lumen. To be more specific, the inner lumen resides in the lower half of the implant so that the denser fluid (the saline solution) will automatically reposition the implant when an individual in whom it is implanted is in a standing, sitting or semi-reclining position.

In the preferred embodiment of the invention, the center of gravity of the saline filled inner lumen lies on or near the lower quartile of the outer lumen when the implant is properly positioned with an individual in a standing or seated position. In its preferred form at least 75% of the volume of the inner lumen is below the center of gravity of the outer lumen. It is also believed that the distance between the center of gravity of the inner lumen and the center of gravity of the outer lumen is at least about 20% of the length of the longest dimension of a generally oval implant.

Figure 2:
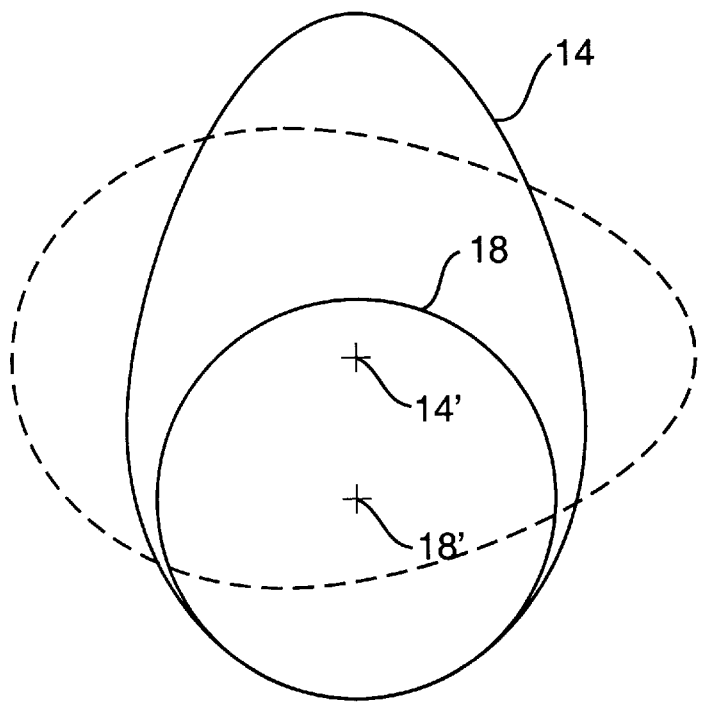
FIG. 2 is a schematic front view of a mammary prosthesis in accordance with the first embodiment of the invention.

As shown by dotted lines in FIG. 2, an implant may become misaligned during athletic or other activities or when an individual is sleeping. However, when the individual returns to a sitting or upright position, the implant is rotated due to the effect of gravity on the denser of the fluid materials and the distance between the center of gravities of the inner and outer lumens.

Figure 3:
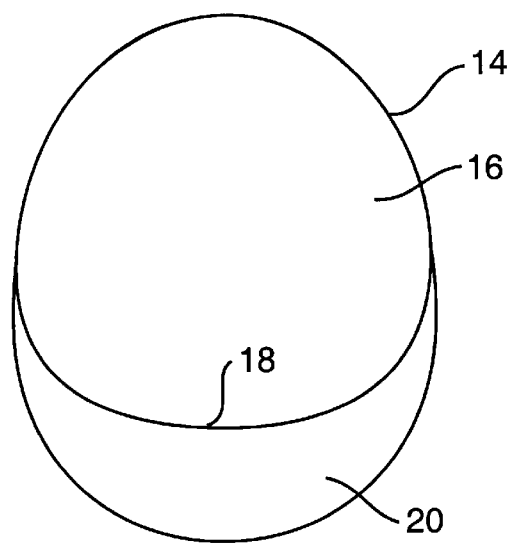
FIG. 3 is a schematic front view of a mammary prosthesis in accordance with a second embodiment of this invention.

In a preferred embodiment of the invention, the outer envelope 14 defines a generally tear-drop shape while the inner envelope 18 has a generally crescent shape as illustrated in FIG. 3. As illustrated therein, the mass of the saline filled inner lumen is adjacent to or relatively close to the bottom of the implant 10 while the crescent shape contributes to the desired shape. Having the mass of the saline solution adjacent to or near the bottom of the implant is believed to optimize the self-positioning feature of the invention.

Figure 4:
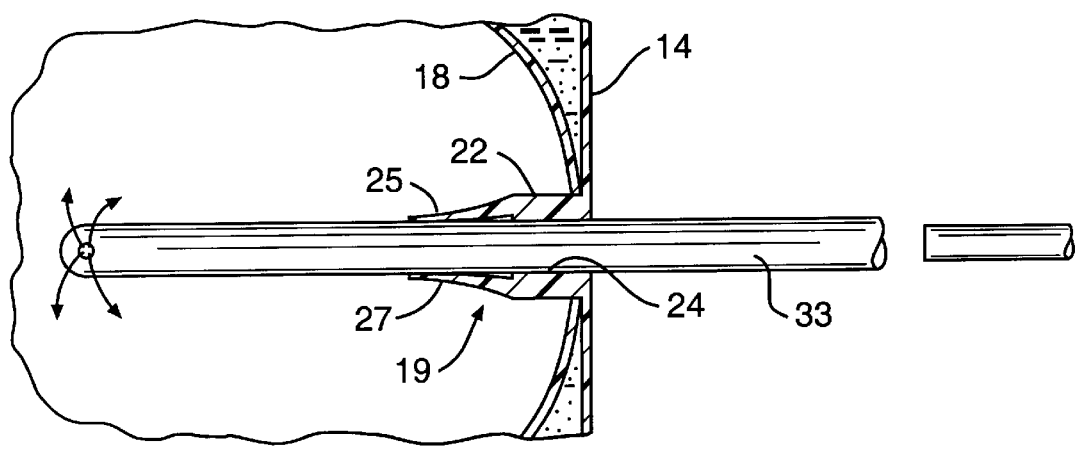
FIG. 4 is an enlarged sectional view which illustrates a self-sealing valve as incorporated in a further embodiment of the invention.

A further embodiment of the invention includes means for adding or removing saline solution to or from the inner lumen. One such means is illustrated in FIG. 4. As shown therein, the outer envelope 14 and inner envelope 18 are fixed together and include a self-sealing valve 19. The valve 19 includes a short connecting tube 22 which surround an opening 24 in the envelopes 14 and 18 and extend inwardly thereof. A pair of opposed flaps 25 and 27 extend inwardly of and surround the tube 22.

A filling tube 33 is preferably of a relatively soft material so as not to puncture the envelopes. The filling tube 33 is shown in an inserted position within the inner lumen and can be inserted at the time of manufacture. Alternatively, a filling tube can be inserted later. In either case, the filling tube 33 extends through the opening 24 in tube 22 and flaps 25, 27. The distal end of the tube 33 is connected with a source of saline solution (not shown) and used to fill the inner lumen with liquid. Upon completion of the filling and expansion process, the filling tube 33 is removed and the self-sealing valve closes. A more detailed description of the self-sealing valves and inflation are disclosed in my previously mentioned U.S. Pat. No. 4,944,749.

A further description of an inflatable permanent implant having a detachable filling tube is contained in my earlier U.S. Pat. No. 4,643,733 which is also incorporated herein in its entirety by reference.

Figure 5:
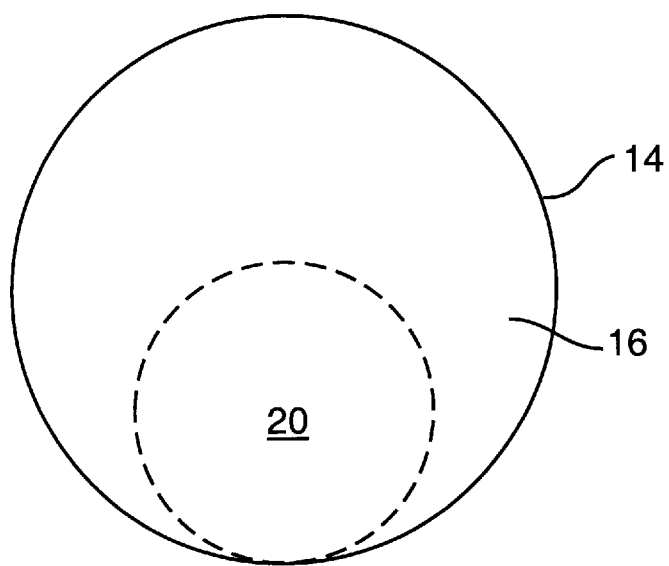
FIG. 5 is a schematic front view of a mammary prothesis in accordance with a further embodiment of the invention.
Figure 6:
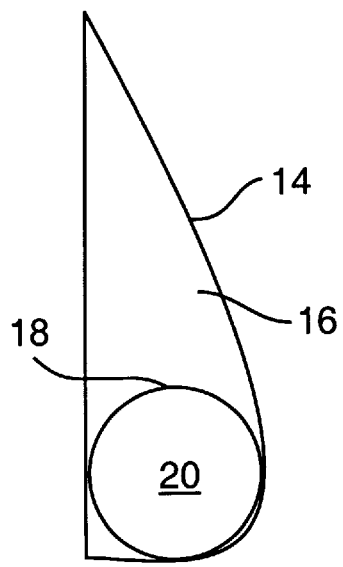
FIG. 6 is a schematic side view of the mammary prothesis shown in FIG. 5.

FIG. 5 shows a mammary prothesis or breast implant 10 in accordance with a further embodiment of the invention. In that embodiment, the implant 10 has a generally round shape or outline profile as, for example, before implantation when laid on a horizontal surface. That same implant after implantation forms a generally tear drop shape when the individual recipient is in a standing or sitting position as shown in FIG. 6.

While the invention has been disclosed in connection with its preferred embodiments, it should be recognized and understood that changes and modifications may be made therein without departing from the scope of the appended claims.

What is claimed is:

1. A self-positioning multi-lumen mammary prosthesis for surgical implantation with a predetermined orientation within a human body comprising:

an outer closed envelope of medical grade elastomer with upper and lower portions, and a first fluid material of a given density contained in said outer closed envelope; and an inner closed envelope of medical grade elastomer disposed within said outer closed envelope and fixed thereto in the lower portion thereof, and said inner closed envelope containing a second fluid material of a given density which is greater than said density of said first fluid material; and, said inner closed envelope containing said second fluid material of a given density being fixed within said lower portion of said outer closed envelope with the center of gravity of said inner closed envelope containing said second fluid below the center of gravity of said outer closed envelope containing said first fluid material;

whereby the mammary prosthesis is maintained in or returned to its predetermined position by the higher density of the second fluid material which is the lower portion of said outer closed envelope.

2. A self-positioning multi-lumen mammary prosthesis for surgical implantation with a predetermined orientation within a human body in accordance with claim 1 in which said outer closed envelope defines a generally oval or generally tear shape.

3. A self-positioning multi-lumen mammary prosthesis for surgical implantation with a predetermined orientation within a human body in accordance with claim 1 in which said first fluid material is a gel and in which said second fluid material is a saline solution.

4. A self-positioning multi-lumen mammary prosthesis for surgical implantation with a predetermined orientation within a human body in accordance with claim 3 in which said first fluid material is a silicone gel.

5. A self-positioning multi-lumen mammary prosthesis for surgical implantation with a predetermined orientation within a human body in accordance with claim 3 in which said first fluid material is a hydrogel.

6. A self-positioning multi-lumen mammary prosthesis for surgical implantation with a predetermined orientation within a human body in accordance with claim 3 in which essentially all of said inner closed envelope is disposed below the center of gravity of said outer closed envelope.

7. A self-positioning multi-lumen mammary prosthesis for surgical implantation with a predetermined orientation within a human body in accordance with claim 3 in which said inner closed envelope defines a generally crescent shape.

8. A self-positioning multi-lumen mammary prosthesis for surgical implantation with a predetermined orientation within a human body in accordance with claim 7 in which the lower portion of said outer closed envelope defines a shape that conforms with the crescent shape of said inner closed envelope.

9. A self-positioning multi-lumen mammary prosthesis for surgical implantation with a predetermined orientation within a human body in accordance with claim 3 in which said inner closed envelope defines a generally spherical shape.

10. A self-positioning multi-lumen mammary prosthesis for surgical implantation with a predetermined orientation within a human body in accordance with claim 3 in which the inner closed envelope essentially fills the lower portion of said outer closed envelope.

11. A self-positioning multi-lumen mammary prosthesis for surgical implantation with a predetermined orientation within a human body in accordance with claim 3 in which said inner and outer closed envelope each include a resealable opening to allow a surgeon to add saline solution to said inner closed envelope.

12. A self-positioning multi-lumen mammary prosthesis for surgical implantation with a predetermined orientation within a human body in accordance with claim 3 in which outer closed envelope of medical grade elastomer has a smooth non-textured surface.

13. A self-positioning multi-lumen mammary prosthesis for surgical implantation within a predetermined orientation within a human body in accordance with claim 1 wherein at least 75% of the volume of said inner closed envelope containing said second fluid material is below the center of gravity of said outer closed envelope containing said first fluid material.

14. A self-positioning multi-lumen mammary prosthesis for surgical implantation within a predetermined orientation within a human body in accordance with claim 1 wherein the distance between the center of gravity of said inner closed envelope containing said second fluid material and the center of gravity of said outer closed envelope containing said first fluid material is at least 20% of the length of the longest dimension of the prosthesis.

* * * * *